United States Patent [19]

Alter et al.

[11] 4,251,671

[45] Feb. 17, 1981

[54] EXTRACTION OF CITRIC ACID

[75] Inventors: John E. Alter, Elkhart, Ind.; Ruth Blumberg, Haifa, Israel

[73] Assignee: Miles Laboratories, Inc., Elkhart, Ind.

[21] Appl. No.: 82,078

[22] Filed: Oct. 5, 1979

[51] Int. Cl.$^3$ .................... C07C 51/48; C07C 59/265
[52] U.S. Cl. .................................. 562/580; 562/513; 562/584
[58] Field of Search ................... 562/580, 584, 513

[56] References Cited

FOREIGN PATENT DOCUMENTS 874030  8/1961  United Kingdom .................... 562/580

*Primary Examiner*—Vivian Garner
*Attorney, Agent, or Firm*—Louis E. Davidson

[57] ABSTRACT

Citric acid can be extracted from aqueous citric acid solutions by contacting such solutions with an N-substituted alkyl amide containing a total of at least twelve carbon atoms.

7 Claims, No Drawings

EXTRACTION OF CITRIC ACID

BACKGROUND AND PRIOR ART

Citric acid has been commercially removed from aqueous solutions thereof, such as fermentation beer, by the procedure of adding lime to form a precipitate of calcium citrate and then reacting the calcium citrate with aqueous sulfuric acid to form citric acid solution and insoluble calcium sulfate. This procedure has the disadvantages of requiring expendable lime and sulfuric acid as well as disposal of calcium sulfate.

Liquid-liquid extraction procedures have also been proposed in the prior art. Amines, mixtures of amines and hydrocarbons, and amine salts have been proposed. One commercial procedure employs a mixture of amines and hydrocarbons, for example, and is disclosed in British Pat. No. 1,426,018. The recovery of citrate salts using an amine-organic solvent mixture for extraction of citric acid is also disclosed in U.S. Pat. No. 3,944,606.

U.S. Pat. No. 3,304,157 discloses the use of various amides, including alkyl amides, for extraction of phosphoric acid. It is known, however, that some materials, such as alcohols, which are suitable for the extraction of phosphoric acid are not suitable for extraction of citric acid.

None of the known prior art discloses or suggests the use of N-substituted alkyl amides for the extraction of citric acid.

SUMMARY OF THE INVENTION

In accordance with the present invention a process for the extraction of citric acid from an aqueous citric acid solution is provided which comprises contacting such solution with an N-substituted alkyl amide containing a total of at least twelve carbon atoms.

DESCRIPTION OF THE INVENTION

The aqueous citric acid solutions used as starting material for the process of the present invention are well known. They can be fermentor beers produced by the fermentation of various cultures, such as Aspergillus niger on carbohydrates, or they can be citric acid solutions obtained from any other source. The concentration of citric acid is not critical.

The N-substituted alkyl amides useful in the present invention are well-known materials which are liquid at 30° C. or below and which are substantially insoluble in water. They have the structural formula

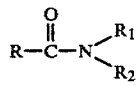

wherein R, $R_1$ and $R_2$ may be the same or different alkyl radicals. R, $R_1$ and $R_2$ can be, for example, methyl, ethyl, propyl, isopropyl, butyl, pentyl, decyl, dodecyl, icosodecyl and the like. The particular alkyl radicals are selected so that the compound formula contains a total of at least twelve carbon atoms. If the compound formula contains less than about twelve carbon atoms, it will have an undesirable solubility in water. Mixtures of these compounds can also be used. These compounds can be prepared by well-known methods.

The extraction process is carried out at a temperature of 10° to 70° C. The extraction conditions are not narrowly critical. Volume ratios of citric acid: alkyl amide of from 0.3:1 to 50:1 have been used. Preferred volume ratios are from 1:5 to 5:1.

The citric acid can be conveniently recovered from the N-substituted alkyl amide phase by back-extraction with water. The conditions for such back-extraction are not narrowly critical.

The invention is described in further detail in the following examples.

EXAMPLE 1

A 50 g. portion of 20 weight percent aqueous citric acid solution was mixed at 30° C. with 1 ml. N,N-diethyldodecanamide (R is $CH_3(CH_2)_{10}-$; $R_1$ and $R_2$ are ethyl) to form an organic phase. This organic phase was analyzed to contain 6.39 weight percent citric acid and 2.97 weight percent water. The aqueous citric acid content of the organic phase contained 68.3 weight percent citric acid by calculation. This shows an extraction of citric acid by the amide.

EXAMPLE 2

The above procedure of Example 1 was repeated using 32 weight percent aqueous citric acid. The organic amide phase was analyzed and the aqueous citric acid content calculated to contain 75.6 weight percent citric acid. This shows an extraction of citric acid by the amide.

EXAMPLE 3

The procedures of Examples 1 and 2 above were repeated at 70° C. to indicate the aqueous citric acid contents of the organic amide phases to contain 54.7 and 68.3 weight percent citric acid, respectively. Here again, this shows an extraction of citric acid by the amide.

EXAMPLE 4

A 45 ml. portion of 20 weight percent aqueous citric acid and a 45 ml. portion of 32 weight percent aqueous citric acid were each individually mixed with 5 ml. of diisopropyldodecanamide (R is $CH_3(CH_2)_{10}-$; $R_1$ and $R_2$ are isopropyl). They were shaken and left to equilibrate at 30° C. overnight. Analyses of the resulting organic phases indicated that the 20 weight percent starting material produced an organic phase containing 1.95 weight percent citric acid and 0.94 weight percent water, and the 32 weight percent starting material produced an organic phase containing 3.9 weight percent citric acid and 2.5 weight percent water. This shows that the amide extracts citric acid and does not extract much water.

EXAMPLE 5

A 45 ml. portion of 20 weight percent aqueous citric acid and a 45 ml. portion of 32 weight percent aqueous citric acid were each individually mixed with 5 ml. of N,N-didodecylacetamide (R is methyl; $R_1$ and $R_2$ are $CH_3(CH_2)_{11}-$). They were shaken and left to equilibrate overnight at 30° C. Analyses of the resulting organic phases indicated that the 20 weight percent starting material produced an organic phase containing 3.23 weight percent citric acid and 1.5 weight percent water, and the 32 weight percent starting material produced an organic phase containing 4.3 weight percent citric acid and 2.3 weight percent water. This shows that the amide produced extraction and separation of citric acid.

EXAMPLE 6

Aqueous solutions containing 0.5, 1, 5, 10, 20 and 32 weight percent citric acid were prepared. A 45 ml. portion of each was extracted with a separate 5 ml. portion of N,N-diethyldodecanamide at 10° C. The organic phases were analyzed to contain the following amounts of citric acid.

| Starting Solution Wt. % Citric acid) | Organic Phase (Wt. % Citric acid) |
|---|---|
| .5 | 0.438 |
|  | 0.875 |
|  | 2.93 |
| 0 | 5.1 |
| :0 | 7.6 |
| .2 | 12.0 |

This shows that the relative concentration of citric acid in the solvent increases with the dilution of the starting material. Thus this process can be used to remove all citric acid from very dilute solutions.

EXAMPLE 7

A 75 ml. portion of 17 weight percent aqueous citric acid solution was extracted at 22° C. with 75 ml. of N,N-diethyldodecanamide. This solvent was then contacted a second time with a fresh 75 ml. portion of the above citric acid solution. The organic solvent was analyzed to contain 6.75 weight percent citric acid.

The solvent was then divided into two 35 ml. portions. The first portion was back-extracted at 70° C. with 15 ml. water. The water was then contacted with the second portion of the solvent. The resulting aqueous phase was analyzed to contain 15.3 weight percent citric acid. This shows that citric acid can be removed from citric acid solutions by the above amide and then recovered therefrom by back-extraction with water.

EXAMPLE 8

A 30 ml. portion of N,N-diethyldodecanamide was successively contacted with 10 ml. and 20 ml. portions of 17.2 weight percent aqueous citric acid solutions at 20° C. to produce a fraction identified as SI-2 which contained 5.8 weight percent citric acid. A second 30 ml. portion of the above solvent was then successively contacted at 20° C. with the above aqueous citric acid solutions after they had been contacted with the first portion of solvent. The resulting organic fraction was identified as SII-2. A 9 ml. portion of water at 20° C. was successively contacted with the SII-2 and SI-2 fractions to produce an aqueous phase containing 9.5 weight percent citric acid. A fresh 9 ml. portion of water was successively contacted with the above SII-2 and SI-2 fractions after they had been contacted with the first portion of water. This indicated the feasibility of a multiple stage extraction and back-extraction.

Carbonizables in citric acid solutions are measured by contacting 10 ml. concentrated sulfuric acid at 0° C. with 1 ml. of sample (prediluted to obtain a final O.D. in the range of 0.1–0.3) in a test tube in an ice bath. The mixture is shaken, then heated for 1 hour at 90° C. It is cooled to room temperature and the O.D measured at 497 nm. The above citric acid starting material has a carbonizable content represented by an O.D. of 7.85. The back-extract aqueous citric acid had an O.D. of 0.06. This shows that the process of the present invention also purifies citric acid solutions by removing undesirable carbonizables.

EXAMPLE 9

A 20 ml. portion of 20 weight percent aqueous citric acid solution and a 20 ml. portion of 32 weight percent aqueous citric acid solution were each individually mixed with 5 ml. of N,N-dimethyltetradecanamide (R is $CH_3(CH_2)_{12}$—; $R_1$ and $R_2$ are methyl) at 30° C. They were shaken and left to separate at 40° C. Analyses of the resulting organic phases indicated that the 20 weight percent starting material produced an organic phase containing 9.58 weight percent citric acid and 8.30 weight percent water, and the 32 weight percent starting material produced an organic phase containing 15.33 percent citric acid and 10.6 weight percent water. This shows that the amide produced extraction and separation of citric acid.

It is also understood that the back-extraction can employ an aqueous solution of an alkali metal hydroxide, such as sodium hydroxide, to result in the recovery of an alkali citrate such as sodium citrate, instead of citric acid.

What is claimed is:

1. A process for the extraction of citric acid from an aqueous citric acid solution which comprises contacting such solution at a temperature of 10° to 70° C. with an N-substituted alkyl amide containing a total of at least twelve carbon atoms and having the structural formula

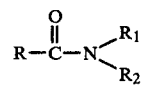

wherein R, $R_1$ and $R_2$ may be the same or different alkyl radicals.

2. A process according to claim 1 wherein R is $CH_3(CH_2)_{10}$— and $R_1$ and $R_2$ are each ethyl.

3. A process according to claim 1 wherein R is $CH_3(CH_2)_{10}$— and $R_1$ and $R_2$ are isopropyl.

4. A process according to claim 1 wherein R is methyl and $R_1$ and $R_2$ are each $CH_3(CH_2)_{11}$—.

5. A process according to claim 1 wherein R is $CH_3(CH_2)_{12}$— and $R_1$ and $R_2$ are each methyl.

6. A process according to claim 1 wherein the amide is then contacted with water to back-extract and recover citric acid.

7. A process according to claim 1 where the amide is then contacted with an aqueous solution of an alkali metal hydroxide to back-extract and recover an alkali citrate.

* * * * *